(12) United States Patent
Falcon

(10) Patent No.: US 6,200,568 B1
(45) Date of Patent: *Mar. 13, 2001

(54) COMPOSITION AND METHOD OF TREATING CANCER WITH TANNIC ACID AND TANNIN COMPLEXES

(75) Inventor: Juan Falcon, Tampa, FL (US)

(73) Assignee: Atajje, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/907,453

(22) Filed: Aug. 8, 1997

Related U.S. Application Data

(62) Division of application No. 08/398,600, filed on Mar. 3, 1995.

(51) Int. Cl.$^7$ .......................... A61K 35/78; A61K 39/385
(52) U.S. Cl. ............................................. 424/195.1
(58) Field of Search .......................................... 424/195.1

(56) References Cited

PUBLICATIONS

Macartney, J.C. et al., "Intracellular filaments in human cancer cells: a histological study." J. Pathol.(England), vol. 129, No. 1, pp. 13–20, Sep. 1979.

Harlos, J.P. et al., "Comparison between the macrophage electrophoretic mobility (MEM) and the fixed tanned erythrocyte electrophoretic mobility (FTEEM) tests in the detection of cancer." Int.J.Cancer (Denmark), vol. 21, No. 4, pp. 413–417, Apr. 15, 1978.

Perchellet, J.P. et al., "Antitumor–promoting activities of tannic acid, ellagic acid, and several gallic acid derivatives in mouse skin." Basic Life Sci. (US), vol. 59, pp. 783–801, 1992.

Ramanathan, R. et al., "Cytotoxic effect of plant polyphenols and fat–soluble vitamins on malignant human cultured cells." Cancer Lett. (Netherlands), vol. 62, No. 3, pp. 217–224, Mar. 15, 1992.

Athar, Mr. et al., "Effect of dietary tannic acid on epidermal, lung, and forestomach polycyclic aromatic hydrocarbon metabolism and tumorigenicity in Sencar mice." Cancer Res. (US), vol. 49, No. 21, pp. 5784–5788, Nov. 1, 1989.

Dyeb, "An index of tumor chemotherapy." National Institutes of Health (No. 2316), pp. 10–12 and 82, Mar. 1949.

Menke et al., Vebers, Tigrernaehr (1991), 19(1), 71–85 (Abstract Only).*

Leinmueller et al, Vebers, Tigrernaehr (1991), 19(1), 45–70.*

* cited by examiner

*Primary Examiner*—Jerome D. Goldberg
(74) *Attorney, Agent, or Firm*—Gilberto M. Villacorta; Pepper Hamilton LLP

(57) ABSTRACT

A pharmaceutical composition including tannic acid and tannin complexes, and a method of treating cancer with tannic acid and tannin complexes.

14 Claims, No Drawings

COMPOSITION AND METHOD OF TREATING CANCER WITH TANNIC ACID AND TANNIN COMPLEXES

This application is a division of application Ser. No. 08/398,600 filed Mar. 3, 1995.

TECHNICAL FIELD

The present invention relates to a pharmaceutical composition comprising tannic acid or tannin complexes, and a method of treating cancer with tannic acid or tannin complexes.

BACKGROUND ART

Tannic acid and tannin complexes are found in the trunk of any of the plants of the Musaceas Family, i.e., *Musa Paradisiaca, Musa Cavendish Enano,* and related Linneo Classifications.

Tannic acid is known to be useful in a diagnostic test for the detection of cancer. For example, Macartney et al. in *J Pathol* (ENGLAND) September 1979, 129 (1) p13–20, "Intracellular filaments in human cancer cells: a histological study", discloses that the distribution of intracellular filamentous systems in human breast and colonic cancers has been demonstrated by means of the tannic acid-phosphomolybdic acid-milling dye staining technique. Plasma membrane-associated staining is prominent in breast carcinomas and is strongest in anaplastic tumors. Strong staining is also noted in the cells at the margins of the tumors where the malignant cells are invading the surrounding tissues. In colonic carcinomas, filaments are mainly restricted to the terminal web region of the cells but dedifferentiation is accompanied by the development of circumferential staining of the cell membrane. The results are discussed in relation to immunohistochemical and electron microscopic studies of contractile proteins in non-muscle cells.

Harlos et al. in *J Cancer* (DENMARK) Apr. 15, 1978, 21 (4) p 413–7, discloses a "Comparison between the macrophage electrophoretic mobility (MEM) and the fixed tanned erythrocyte electrophoretic mobility (FTEEM) tests in the detection of cancer." When peripheral lymphocytes from patients with a history of cancer are incubated with encephalitogenic factor (EF), in 90% of cases the resulting products reduce the net surface negativity of guinea-pig macrophages, used as detector cells, as revealed in the macrophage electrophoretic mobility (MEM) test. The MEM test is positive in 36% of people with no history of cancer. Formaldehyde-fixed tanned sheep erythrocytes have been used as detector cells in place of guinea-pig macrophages, in a fixed tanned erythrocyte electrophoretic mobility (FTEEM) test, with lymphocyte products identical to those used in MEM tests. In patients with a history of cancer, positive results were obtained in 28/42 cases with the FTEEM test compared with 32/42 in the MEM test. In people with no history of cancer, negative results were obtained in 16/18 cases with the FTEEM test, compared with 12/18 in the MEM test in the present series, and 51/69 in a more extensive series. These differences are not significant. Cases in which discrepancies are revealed between the two tests are discussed in terms of individual case histories.

Tannic acid has been shown to inhibit 12-O-tetra-decanoyl-phorbol-13-acetate (TPA). Perchellet et al., *Basic Life Sci* (UNITED STATES) 1992, 59 p. 783–801, discloses that naturally occurring plant phenols with antimutagenic and anticarcinogenic activities were tested for their abilities to inhibit the biochemical and biological effects of the potent tumor promoter 12-O-tetradecanoyl-phorbol-13-acetate (TPA) in mouse epidermis in vivo. When applied topically to mouse skin, tannic acid (TA), ellagic acid, and several gallic acid derivatives all inhibited TPA-induced ornithine decarboxylase activity, hydroperoxide production, and DNA synthesis, three biochemical markers of skin tumor promotion. In a two-step initiation-promotion protocol, the same phenolic compounds also inhibited the incidence and yield of skin tumors promoted by TPA.

Ramanathan et al. in "Cytotoxic effect of plant polyphenols and fat-soluble vitamins on malignant human cultured cells", *Cancer Lett* (NETHERLANDS) Mar. 15, 1992, 62 (3) p. 217–24, discloses in vitro studies which showed that several flavonoids, tannic acid, gallic acid and fat-soluble vitamins inhibited HeLa and Raji lymphoma cell growth. The inhibition trend exhibited by these compounds was similar for both cell lines, and their growth was inhibited dose dependently. Butein, (10 microM), the most potent anti-proliferative agent, exerted 30% growth inhibition and was more effective on HeLa cells. Retinol (100 microM) inhibited cell proliferation completely. Tannic acid was twice as potent as its monomer gallic acid. From structure-activity consideration, the C 2,3-double bond of the flavonoid molecule was important for activity. Flavonoid aglycones were more effective than their corresponding glycosides in suppressing cell growth in vitro. No in vivo results were presented.

Athar et al., "Effect of dietary tannic acid on epidermal, lung, and forestomach polycyclic aromatic hydrocarbon metabolism and tumorigenicity in Sencar mice," *Cancer Res* (UNITED STATES) Nov. 1, 1989, 49 (21) p. 5784–8, discloses tannic acid inhibits the mutagenicity of several polycyclic aromatic hydrocarbons (PAHs) and their bay-region diol-epoxides. Studies have shown that when applied topically to Sencar mice, tannic acid caused substantial inhibition of epidermal PAH metabolism, subsequent PAH-DNA adduct formation, and PAH-induced skin tumorigenesis. None of the above publications discloses that tannic acid is useful for the treatment of cancer.

Current standard cancer treatments include surgery, chemotherapy and radiation therapy, which often present patients with unpleasant side effects and, depending on the type of cancer may have limited effectiveness as treatments.

There is a need in the art for proven effective treatments for many types of cancer, with limited unpleasant side effects. The tannic acid pharmaceutical composition and method of the present invention overcomes the deficiencies in the prior art compounds.

DISCLOSURE OF THE INVENTION

It is an object of the present invention to provide a pharmaceutical composition for the treatment of cancer comprising tannic acid or tannin complexes from the sap of a plant of the Musaceas Family and a pharmaceutically acceptable carrier. The plant is preferably selected from the group consisting of *Musa paradisiaca* (plantain); *Musa Cavendish Enano* (banana), varieties and mixtures thereof.

It is an object of the present invention to provide a method of treating cancer comprising administering an effective amount of a pharmaceutical composition comprising tannic acid or tannin complexes from natural or synthetic sources. It is preferred that the pharmaceutical composition is administered at least once daily, and more preferred that the composition is administered 4 times daily.

The pharmaceutical composition of the invention is advantageously used to treat any cancer condition. Thus the invention preferably provides a method of treating cancers including, but not limited to bladder, breast, kidney, leukemia, myeloma, liposarcoma, lymphoma, colon, penis, tongue, prostate and uterus cancers.

In an alternative embodiment the invention provides a method of stripping N-acetyl neuraminic acid from a cancer cell surface allowing recognition of the cancer cell by the immune system in vivo comprising contacting said cancer cell with tannic acid or tannin complexes.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DESCRIPTION OF THE INVENTION

The present invention relates to pharmaceutical compositions comprising tannic acid, tannin complexes or mixtures thereof, and a method of treating cancer with tannic acid and tannin complexes. The invention will now be described in a manner to enable production and use of the tannic acid and tannin complex compositions for the treatment of cancer. Tannin complex compositions as used herein means hydrolyzable tannins, such as esters of sugars, usually glucose.

What is known about the cancer cells' adhesion and their invasive and metastatic growth potential in human tumors? Tumor cells produce an outer protective covering which camouflages the cancer cells epitope structure so the immune system cannot recognize the cells. The protective coating contains N-acetylneuraminic acid in a linear homopolymer of 2-8 linked N-acetylneuraminic acid (NeuNAc) which is referred to as polysialic acid (PSA). PSA is expressed on the adhesion molecule NCAM (Neural Cell Adhesion Molecule) and most cell adhesion molecules. In the cancer patient, PSA is found in extremely elevated blood levels as well as bound to erythrocytes and other blood components vital to the immune response.

It has been shown experimentally that PSA-NCAM drastically increases cell to cell distances and decreases the adhesion potential on NCAM. One of the vehicles for this physiological change is the hydrated volume of PSA in PSA-NCAM versus NCAM in adjacent cells. The presence of PSA decreases adhesion via a physical impedance of overall membrane contacts. These modulatory effects of PSA are relevant to cell migration, establishment of temporal cell-cell contacts, and cellular differentiation during embryonic development.

In the cancer patient, the presence of PSA is linked to a loss of adhesion potential which facilitates the invasive and metastatic growth of the tumors as well as potential structural differentiation and reorganization of healthy cells into tumor cells, i.e., neoplastic cells.

PSA is the principal molecule involved in the masking of the tumor-specific antigens (TA) which normally binds to immune system components, decreasing the effectiveness of NCAM and other cell adhesion molecules, and inducing differentiation of healthy cells into neoplasts. Thus, if one can obtain selective removal of PSA from tissues and the bloodstream where possible, the major limitation which makes cancer impossible to cure, outside of operative conditions, would be eliminated. This would allow the body to attack and destroy a tumor in much the same way it rejects a transplanted organ.

The tannic acid and tannic acid complexes in accordance with the present invention binds to and precipitates N-acetylneuraminic acid bound in PSA-NCAM as well as in circulating blood and bound to erythrocytes. Tannic acid recognizes the linear homopolymer of 2-8 linked N-acetyl neuraminic acid, with the exposed amino group at the fifth (5) position, as an amino acid chain (protein).

The valent electrons on the nitrogen group of PSA bind covalently to the carbonyl group of tannic acid, linking the chains of the tannic acid moiety. The resulting bond is a very stable one with several resonance structures. See scheme 1 below.

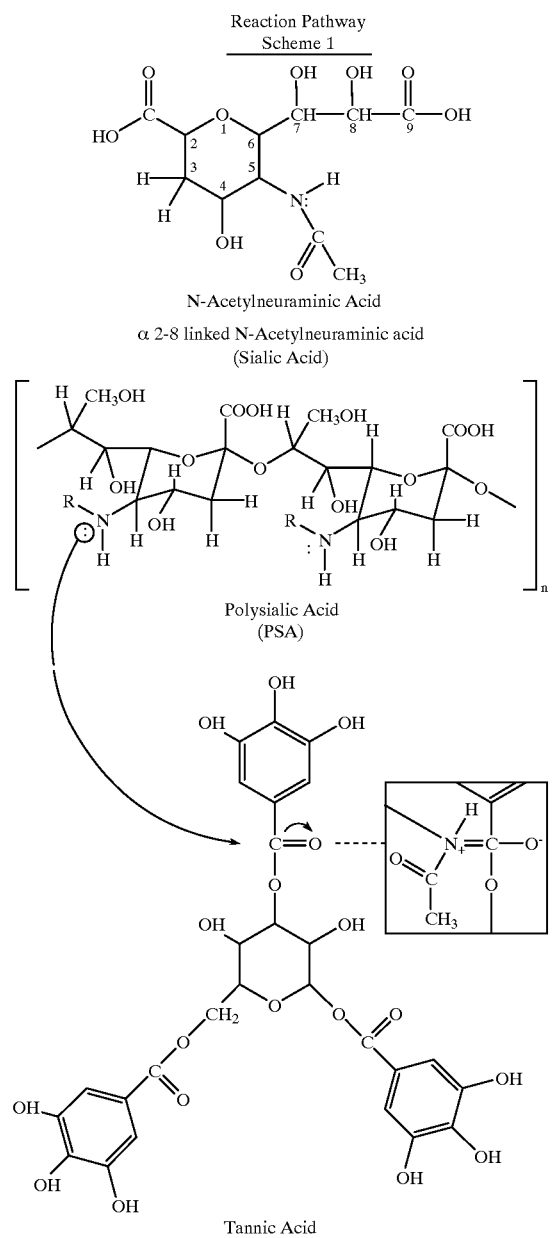

Three moles of N-acetylneuraminic acid are bound to each mole of tannic acid in solution. When this activity is studied, and considering the interesting property of PSA to undergo depolymerization under mildly acidic conditions, this evidences that the reaction between tannic acid and PSA (leading to precipitation of three moles of N-Acetylneuraminic Acid for every mole of tannic acid) is a highly favored and facilitated reaction.

The tannic acid and tannin complexes act by stripping N-Acetyl neuraminic acid from the cell surface moiety. The tannic acid, therefore, acts as an astringent. In so doing, tannic acid and tannin complexes affect the cell changes discussed previously, allowing the body's own immune system to reject cancerous growth in much the same way it rejects any foreign invader.

The tannic acid and tannin complexes of the present invention exposes cancer cell epitopes that were previously camouflaged by the PSA. At the same time tannic acid and tannin complexes elevate the immune response by freeing the circulating blood components from bound PSA.

The most predominant target of PSA in its propagation of an immune deficient condition in cancer patients is the macrophage, a cell that not only phagocytizes unfriendly cells but also activates the cell-mediated and humoral-immune response. It is believed that the cancer cell, by the secretion of N-acetylneuraminic acid and its polymerization into PSA, induces an immune deficiency which is reversed by the action of tannic acid and tannin complexes. No one knows exactly what initiates cancerous growths, but it is the inventors conclusion that cancerous growths induce immune deficiencies.

Method of Production of Tannic Acid Product

Thus the tannic acid and tannin complexes of the present invention may be formulated into a pharmaceutical composition for the treatment of cancer. Tannic acid and tannin complexes in accordance with the present invention may be produced from natural sources or may be produced synthetically. Tannic acid from natural sources is preferred. To obtain tannic acid extract from natural sources, the following procedure is followed.

To obtain the active tannic acid and tannin complexes, the trunk of any of the plants of the Musaceas Family, for example, but not limited to *Musa Paradisiaca, Musa Cavendish Enano*, and related Linneo Classifications, are milled to extract the sap of the plant. The pulp is filtered out of the sap to obtain a clear, characteristic tan liquid.

This liquid is preferably incorporated into a standard pharmaceutical preparation containing as its base: Sorbitol 70% Solution (20.9588%), Cremophor RH40 (partially hydrogenated castor oil)(8.8401%), Potassium sorbate (0.15%), Methylparaben (0.038%), and Propylparaben (0.013%) w/w. The batching procedure is an FDA approved, CGMP, SOP for liquid pharmaceuticals. The total percent of tannic acid or tannin complex in the final product should be about 5–20 percent. Preferably the amount of tannic acid or tannin complex in the final product is about 10–20 percent concentration, most preferred is about 10% tannic acid and/or tannin complex based on total concentration of 100% when the active agent is in the presence of a pharmaceutical carrier.

If the natural sources yield a percentage lower than 10%, a food grade tannic acid may be used to yield a 10% concentration. If the natural source yields a higher percentage than 10%, the product may be diluted and retested to assure a 10% concentration.

To prepare tannic acid and tannin complexes from a synthetic source, the following batching procedure is an FDA approved, CGMP, SOP for liquid pharmaceuticals. Food Grade Tannic Acid is dissolved into water along with the standard pharmaceutical preparation as described under the natural extract. The percent tannic acid in final product is about 10 percent (10%). Tannic acid ($C_{76}H_{52}O_{18}$) may be produced synthetically as described in references cited in the Merck Index 11th Ed., abstract 9023, p. 1431, Merck Publishing Company 1989, (incorporated herein by reference in its entirety).

Further, the pharmaceutical compositions of the present invention are useful in compositions for systemic administration to humans and animals in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient.

Either fluid or solid unit dosage forms can be readily prepared for oral administration. For example, the tannic acid or tannin complex compounds of the invention can be mixed with conventional ingredients such as dicalciumphosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule.

Suspensions, syrups and elixers may be used for oral administration of fluid unit dosage forms. A fluid preparation including oil may be used for oil soluble forms. A vegetable oil such as corn oil, peanut oil or sunflower oil, for example, together with flavoring agents, sweeteners and any preservatives produces an acceptable fluid preparation. A surfactant may be added to water to form a syrup for fluid unit dosages. Hydroalcoholic pharmaceutical preparations may be used having an acceptable sweetener such as sugar, saccharine or a biological sweetener and a flavoring agent in the form of an elixer.

Pharmaceutical compositions for parenteral and suppository administration can also be obtained using techniques standard in the art. The tannic acid and tannin complexes can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like.

Additional formulations for administration may be made in accordance with methods and amounts known in the art as set forth in Remington's Pharmaceutical Sciences, 18th Ed., Wiley Publishing (1990) incorporated herein by reference in its entirety.

Table 1 below represents recommended dosages, methods and times of administration and a preferred pharmaceutical formulation in accordance with the present invention.

TABLE 1

Recommended Dosage if Plantain Syrup

| Catetory | Age | Weight | | Height | | Before meals and at bed time 4 Times a day (ml) | | | |
|---|---|---|---|---|---|---|---|---|---|
| | | Kg | lb. | cm | in. | (1) | (2) | (3) | (4) |
| Infants | 0.5–1.0 | 9 | 20 | 71 | 28 | 4 | 8 | 12 | 16 |
| Children | 1–3 | 13 | 29 | 90 | 35 | 6 | 12 | 17 | 23 |
| | 4–6 | 20 | 44 | 112 | 44 | 9 | 18 | 26 | 35 |
| | 7–10 | 28 | 62 | 132 | 52 | 13 | 25 | 37 | 50 |
| Males | 11–14 | 45 | 99 | 157 | 62 | 40 | 60 | 80 | 120 |
| | 15–18 | 66 | 145 | 176 | 69 | 58 | 87 | 116 | 174 |
| | 19–24 | 72 | 160 | 177 | 70 | 64 | 96 | 128 | 192 |
| | 25–50 | 79 | 174 | 176 | 70 | 70 | 104 | 139 | 209 |
| | 51+ | 77 | 170 | 173 | 68 | 68 | 102 | 136 | 204 |
| Females | 11–14 | 46 | 101 | 157 | 62 | 40 | 61 | 81 | 121 |
| | 15–18 | 55 | 120 | 163 | 64 | 48 | 72 | 96 | 144 |
| | 19–24 | 58 | 128 | 164 | 65 | 51 | 77 | 102 | 153 |
| | 25–50 | 63 | 138 | 163 | 64 | 55 | 83 | 110 | 165 |
| | 51+ | 65 | 143 | 160 | 63 | 57 | 86 | 114 | 171 |

Dosage
1. Cancer Stage 1 and other disorders during the 3 months-used as prophylactic in cancer and other diseases.
2. Cancer Stage 2 and 3 during 3 months and continue with dosage (1) during another 3 months.
3. If the cancer patient has been treated with chemotherapy or radiotherapy this dosage is for three months and three months more with dosage (2). Then three additional months with dosage (1). (9 months in total).
4. Cancer in Stage 4 and terminal care, during a year.
5. All these dosages may be modified by the physician using methods known in the art, after monthly checkup. Dosages range from about 4 to about 200 ml. Maximum dosages for height and weight appear in column 4 above.

Clinical Data

The following clinical data was collected on voluntary patients during clinical experimental trials in Cuba. A 10% concentration of tannic acid was used in all of the clinical studies set forth below.

Patient #1: 79 year old male, Prostate Carcinoma, permanent catheter was surgically inserted. Cancer was inoperative because of cardiovascular condition. Therapy in accordance with the present invention was administered at the maximum dosage for the initial three month period according to "dosage administration." Two weeks after initiation of therapy in accordance with the invention catheter was removed. Cancer was cured and the patient returned to normal activities with the first treatment period, three months. After that, he used the product for 7 additional months.

Patient #2: 43 year old female, Breast carcinoma. Surgery was performed Jan. 11, 1982 on left breast. The problem of metastatic growth was a concern. Therapy in accordance with the invention was initiated for a minimal 3 month period based on patient weight, height criteria. No additional cancerous growths were detected anywhere in her body.

Patient #3: 51 year old female, Breast Carcinoma. Cancer diagnosed at the Cancer Institute of Havana in the left breast. Tumor measured 5 cms by 5 cms. Patient refused removal of breast and therapy in accordance the invention was administered. Therapy in accordance with the invention was initiated based on weight/height criteria at maximum levels (see Table 1, column 4). Tumor diminished in size after first three month interval to the point where it was very difficult to detect by manual examination. Therapy in accordance with the invention continued according to "dosage administration" for a period of one year. Cancer never returned to this day.

Patient #4: 54 year old female, Colon Carcinoma. She was administered 72 chemotherapy dosages simultaneously with the therapy in accordance with the invention. Her blood work throughout the chemotherapy/therapy was normal. She continued regular checkups and all have been negative. Maximum therapy in accordance with the invention was administered along with the chemotherapy.

Patient #5: 52 year old female, Carcinoma of the uterus. Surgery to remove the uterus was recommended and an operation planned. Upon opening patient, metastatic growth throughout internal organs was detected. Uterus was not removed and patient was classified terminal. Maximum therapy in accordance with the invention levels were administered for a period of one year. She was cured of the cancer throughout her body. Yearly checkups have confirmed no relapse.

Patient #6: 50 year old female. Breast Carcinoma. Operated for removal of left mammary gland in 1981. In 1982 they found the right mammary gland was also infected with cancer. Operation to remove was not an option because metastasis was detected in the skeletal system, lungs and the liver. She was classified terminal. Maximum therapy in accordance with the invention was applied for a period of one year, in which time, she was cured of cancer in all organs. Semi-annual check-ups reveal no relapse.

Patient #7: 67 year old female. Carcinoma of the uterus. Cancer was pervasive throughout organ. Radiation therapy was prescribed. She had such a violent reaction to the radiation that she refused further treatment. She underwent therapy in accordance with the invention at maximum dosage for a period of one year. No other treatments were applied. Semi-annual checkups reveal no relapse.

Patient #8: 2 year old boy. Acute Lymphocytic Leukemia. Patient classified as terminal. Therapy in accordance with the invention was initiated by drop-wise administration because patient was having difficulty swallowing. Administration was continued until patient was able to swallow dosage after 1 week. Therapy period was one year at maximum dosage as per weight/height criteria. Patient initially showed signs of being cured. Relapse occurred two years after completion of therapy through a process where the leukemia cells encysted in the testes. Cyst ruptured at the time of relapse. Therapy in accordance with the invention was readministered and patient was cured through a year long treatment period. To this date, all check-ups have been negative. Patient is now 17 years old.

Patient #9: 56 year old female. Colon Carcinoma. Experienced bowel blockage. Diverted passage of refuse but did not remove tumor. Tumor was so large that removal was not feasible. Surgery was performed to extend her life without hope of cure. Doctors opted to bypass chemotherapy and radiation therapy fearing results of extended therapy would be devastating. Therapy in accordance with the invention was administered at maximum level for a period of one year. Tumor disappeared and has not returned.

Patient #10: 38 year old female. Cancerous Lesion of the Tongue. The lesion was about the size of a penny. Over the course of six months, conventional treatment was ineffective. The lesion grew deeper into the tongue. Therapy in accordance with the invention was administered over 3 months at stage 1 with weight/height criteria. The lesion healed and the tissue of the tongue was restored to normal. No relapse.

Patient #11: 64 year old male. Carcinoma of penis. Surgery was performed to remove sexual organs (testes and penis). They found that the cancer metastasized and the patient was classified terminal. Therapy in accordance with the invention was administered at maximum levels immediately after surgery for one year. He has had no relapse and is cured of the cancer that was diagnosed after his surgery.

Patient #12: 5 year old boy. Acute Lymphocytic Leukemia. Therapy in accordance with the invention was administered at maximum level according to weight/height criteria for one year. Patient initially showed signs of being cured. Relapse occurred about 2 years after completion of therapy in accordance with the invention through a process where the leukemia cells encysted in the testes. Cysts ruptured at the time of relapse. As in Patient #8, therapy in accordance with the invention was readministered through a period of one year. Patient was cured and subsequent check-ups have been negative. Patient is now 20 years old.

Patient #13: 4 year old female. Acute Lymphocytic Leukemia. Chemotherapy had been administered. The patient's overall reaction to the chemotherapy was very violent. There was no improvement with the chemotherapy. Therapy in accordance with the invention was administered and immediately overall bloodwork returned to normal parameters. Therapy in accordance with the invention was administered for one year at maximum levels according to weight/height criteria. Patient (now 19 and married) was cured of cancer and no relapse has occurred.

Patient #14: 21 year old male. Hodgkin's Lymphoma. Chemotherapy was initially applied with no improvement to condition of the disease and a devastating reaction to the chemotherapy. On patient's authority, chemotherapy was discontinued and therapy in accordance with the invention was administered according to weight/height criteria for one year. Even though patient was considered terminal prior to therapy in accordance with the invention, he was cured of disease. Subsequent check-ups have been negative and no relapse has been recorded.

Patient #15: 58 year old female. Breast carcinoma. Left mammary gland was removed and because of fear of metastasis, therapy in accordance with the invention was administered for a period of one year according to weight/height criteria. At the end of the therapy in accordance with the invention, no cancer was detected. Two years after therapy in accordance with the invention on yearly check-ups, it was discovered that she had carcinoma of the uterus. Therapy in accordance with the invention was readministered for a period of one year. She was cured of uterine cancer and ongoing check-ups have been negative. Great concern was expressed about the possibility of metastasis but none occurred.

Patient #16: 59 year old female. Carcinoma of the Breast with metastasis in both lungs and lymph nodes. Attending physician detected cancer initially in the lungs, but primary site was in the breast. Patient was classified terminal. Therapy in accordance with the invention was administered at maximum levels according to weight/height criteria for a period of one and one half year. At the end of therapy in accordance with the invention, the Doctor declared patient cured, and was impressed by the therapy. All check-ups have since been negative for cancer.

Patient #17: 4 year old female. Monoblastic Leukemia. Chemotherapy was administered with no improvement to her condition, but devastating to her well being. Oral chemotherapy maintenance was discontinued by parents with only the three month periodic treatment at ongoing check-ups. No improvement to her condition was reported. Therapy in accordance with the invention was initiated at maximum levels according to weight/height criteria for a period of one year. She was cured of monoblastic Leukemia and has had no relapse.

Patient #18: 41 year old female. Liposarcoma of the right thigh. She underwent two unsuccessful operations to remove cancer with condition returning each time. Amputation was recommended for patient's survival, but patient refused. Therapy in accordance with the invention was administered at maximum levels according to weight/height criteria for a period of one year. She was cured of cancer, and has had no relapse. Patient is 54 years old and doing well.

Patient #19: 51 year old female. Multiple Myelomas. Patient was unable to walk due to metastasis in hips and ribs. No other therapy was administered but the therapy which was given at maximum levels for a three month period. Doctors examined X-rays taken at the end of the therapy, and all concurred on actual regeneration of skeletal tissue and structure. Patient's family never revealed to her that she had cancer. The therapy was designed for a one year period, but patient refused treatment after three months because she had gained weight. Patient died four years later of Myeloma.

Patient #20: 30 year old male. Hypernephroma (Cancer of Kidney). The Chief of Oncology and patient's relative were the attending physicians. Metastasis occurred in both the lungs and ribs (liver and brain were also suspected). Patient was given less than one month to live and was classified terminal. Therapy in accordance with the invention was administered at maximum levels according to weight/height criteria for a period of one year. After 20 days of therapy in accordance with the invention, regeneration of ribs had occurred, and after one month the patient had returned to normal daily activities. At three months, the therapy was discontinued due to matters beyond patient's control. The patient lived for two years after therapy, and never experienced any pain from the relapse.

Patient #21: 27 year old male. Carcinoma of the Bladder. Patient was the first to receive therapy (in 1951). Attending Urologist, diagnosed carcinoma which was confirmed by two other physicians. All three physicians performed a cystoscopic examination. The carcinoma was located on the right wall of the neck of the bladder. Patient's symptoms were painful urination with high levels of blood in urine. Surgery was recommended by all three physicians. Patient refused surgery and therapy in accordance with the invention was administered at maximum dosage according to weight/height criteria. Regular three month check-ups were performed which included a cystoscopic exam each time, and at the first check-up the carcinoma had diminished in size. At 10 months, patient was released from physicians care and declared cured of cancer spontaneously (physicians were unaware of therapy). The patient married a short time later, had four healthy children, and is currently 71 years old and has suffered no relapses.

In sum, the invention provides a pharmaceutical composition including tannic acid and tannin complexes, and a method of treating cancer with tannic acid and tannin complexes which shows effective results in the treatment of cancer.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A method of treating a cancer sensitive to tannin complexes, in a patient in need thereof, comprising administering an effective amount of a pharmaceutical composition comprising tannin complexes
wherein the cancer is selected from the group consisting of: prostate carcinoma, breast carcinoma, colon carcinoma, carcinoma of the uterus, acute lymphocytic leukemia, cancerous lesion of the tongue, carcinoma of the penis, Hodgkins' lymphoma, monoblastic leukemia, liposarcoma, multiple myeloma bladder cancer, and hypernephroma.

2. The method of treating cancer according to claim 1, wherein said pharmaceutical composition comprises about 5–20% tannin complexes.

3. The method of treating cancer according to claim 1, wherein said pharmaceutical composition comprises about 10% tannin complexes.

4. The method of treating cancer according to claim 1, wherein said pharmaceutical composition is administered at least once daily.

5. The method of treating cancer according to claim 4, wherein said pharmaceutical composition is administered four times daily.

6. The method of treating cancer according to claim 1, wherein said pharmaceutical composition further comprises gallic acid.

7. The method of treating cancer according to claim 1, wherein the tannin complexes are derived from the sap of a plant of the Musaceas Family.

8. The method of treating cancer according to claim 1, wherein said effective amount comprises about 2.5–5% tannin complexes.

9. The method of treating cancer according to claim 1, wherein the tannin complexes are derived from an extract of a plant of the Musaceas Family.

10. A method of treating a cancer sensitive to tannin complexes, in a patient in need thereof, comprising administering an effective amount of a pharmaceutical composition comprising tannin complexes.

11. A method of stripping N-acetyl neuraminic acid from a cancer cell surface allowing recognition of said cancer cell by the immune system in vivo comprising contacting said cancer cell with an effective amount of tannic complexes, wherein the cancer is selected from the group consisting of: prostate carcinoma, breast carcinoma, colon carcinoma, carcinoma of the uterus, acute lymphocytic leukemia, cancerous lesion of the tongue, carcinoma of the penis, Hodgkin's lymphoma, monoblastic leukemia, liposarcoma, multiple myeloma, and hypernephroma.

12. The method of stripping N-acetyl neuraminic acid from a cancer cell surface allowing recognition of said cancer cell by the immune system in vivo according to claim 6, wherein the tannin complexes are derived from the sap of a plant of the Musaceas Family.

13. The method of stripping N-acetyl neuraminic acid from a cancer cell surface allowing recognition of said cancer cell by the immune system in vivo according to claim 6, wherein the tannin complexes are derived from an extract of a plant of the Musaceas Family.

14. A method of stripping N-acetyl neuraminic acid from a cancer cell surface allowing recognition of said cancer cell by the immune system in vivo comprising contacting said cancer cell with an effective amount of tannic complexes.

* * * * *